(12) United States Patent
Elsamahy

(10) Patent No.: US 9,925,358 B2
(45) Date of Patent: Mar. 27, 2018

(54) CATHETER STABILIZATION DEVICE AND METHOD OF USE

(71) Applicant: Tamer Elsamahy, Boca Raton, FL (US)

(72) Inventor: Tamer Elsamahy, Boca Raton, FL (US)

( * ) Notice: Subject to any disclaimer, the term of this patent is extended or adjusted under 35 U.S.C. 154(b) by 0 days.

(21) Appl. No.: 15/464,177

(22) Filed: Mar. 20, 2017

(65) Prior Publication Data

US 2017/0189647 A1 Jul. 6, 2017

Related U.S. Application Data

(63) Continuation of application No. PCT/US2016/026471, filed on Apr. 7, 2016.

(60) Provisional application No. 62/143,893, filed on Apr. 7, 2015.

(51) Int. Cl.
*A61M 31/00* (2006.01)
*A61M 5/32* (2006.01)
*A61M 25/02* (2006.01)

(52) U.S. Cl.
CPC ..... *A61M 25/02* (2013.01); *A61M 2025/0246* (2013.01); *A61M 2025/0273* (2013.01); *A61M 2205/584* (2013.01)

(58) Field of Classification Search
CPC .. A61M 2025/0246; A61M 2025/0273; A61M 2205/584; A61M 25/02
USPC ........................................... 604/500
See application file for complete search history.

(56) References Cited

U.S. PATENT DOCUMENTS

| 5,300,037 A * | 4/1994 | Delk ............... A61M 25/02 128/DIG. 26 |
| 5,468,231 A | 11/1995 | Newman et al. |
| 6,124,521 A | 9/2000 | Roberts |
| 2014/0005607 A1 * | 1/2014 | Elsamahy .......... A61M 25/02 604/180 |

* cited by examiner

*Primary Examiner* — Jason Flick
(74) *Attorney, Agent, or Firm* — Johnson | Dalal; Mark C. Johnson

(57) ABSTRACT

A catheter stabilization device having a release liner and a catheter stabilization member with a permeable first layer and a bottom surface having an adhesive interposed between the release liner and the first layer. The catheter stabilization member includes an elongated continuous retention strip coupled to the first layer is of a deformably rigid material operably configured to have a first static state with a first shape, a dynamic state, generated by an external force, with a second shape different than the first shape, and a second static state, after removal of the external force, with the second shape in a fixed configuration.

20 Claims, 7 Drawing Sheets

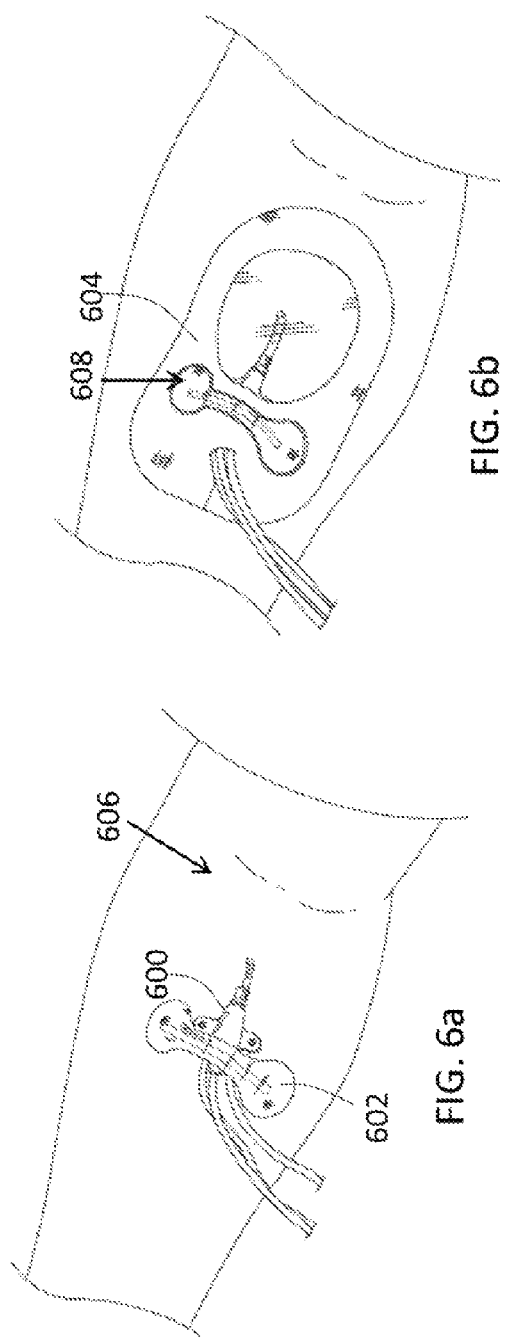
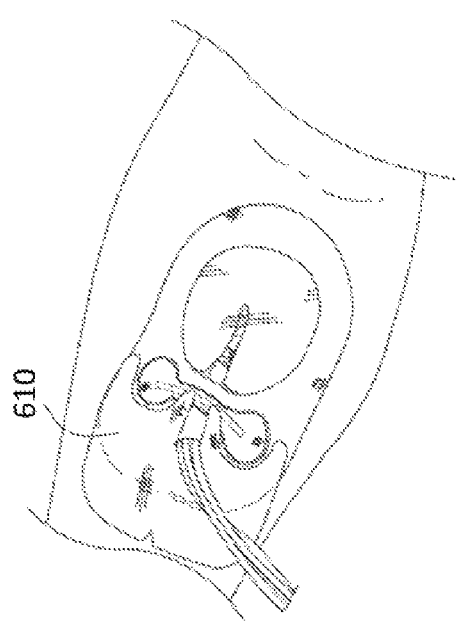
FIG. 6a
FIG. 6b
FIG. 6c

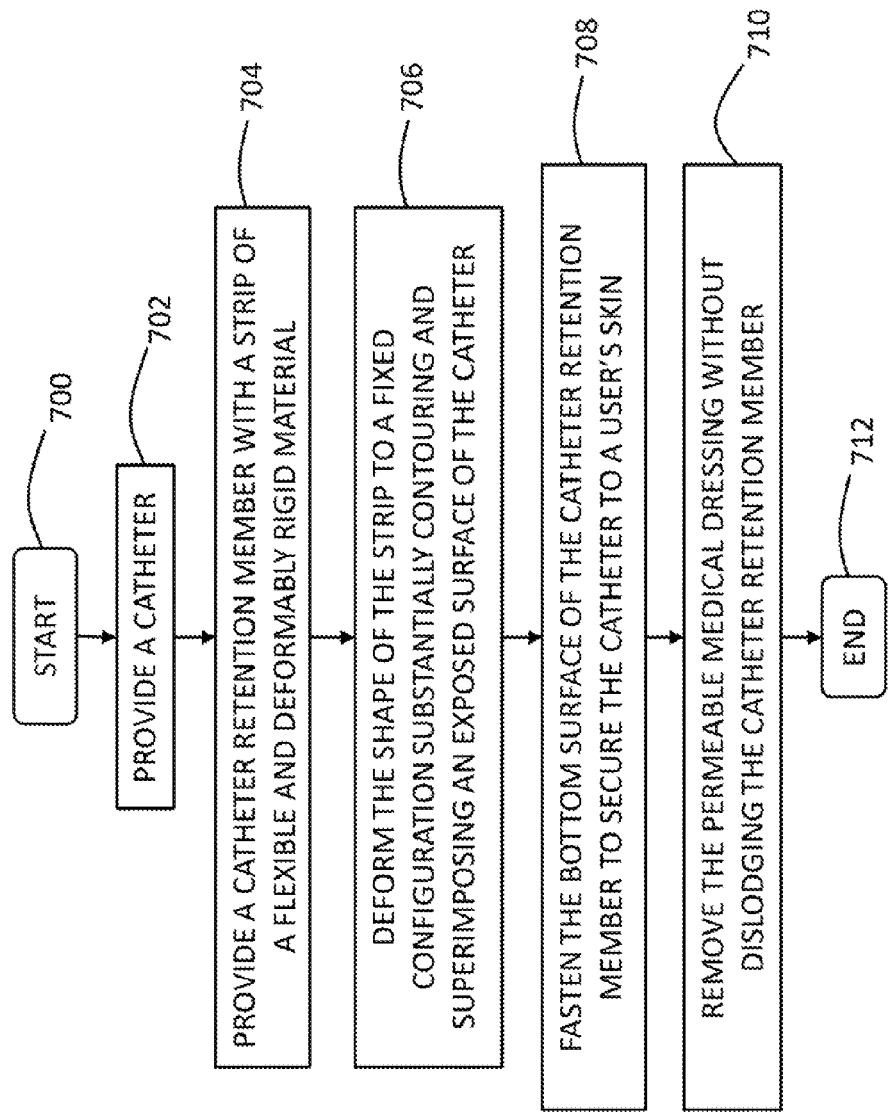

CATHETER STABILIZATION DEVICE AND METHOD OF USE

CROSS-REFERENCE TO RELATED APPLICATION

This application claims priority to PCT Application No. PCT/US16/26471 filed Apr. 7, 2016, which claims priority to U.S. Provisional Patent Application No. 62/143,893, filed Apr. 7, 2015, the entirety of both are incorporated herein by reference.

FIELD OF THE INVENTION

The present invention relates generally to methods and devices used to stabilize one or more medical tubings, more particularly, a catheter, to a patient.

BACKGROUND OF THE INVENTION

In anticipation of various medical procedures, or even for use with certain medical procedures, catheter(s), and other medical tubing are utilized by many individuals. These devices are principally used to provide a passageway into a user's body for insertion of medical instruments, administration of fluids and gases, and drainage or measurements of a user's bodily fluid(s), among other uses. Some exemplary catheters include peripheral intravenous catheters (PIVCs), peripherally inserted central catheters (PICCs), central venous catheters (CVCs), implantable ports, Huber needles, dialysis catheters, among others.

After the catheterization process, or the act of inserting a catheter into a user's body is complete, ensuring the catheter is stabilized is one of the most essential requirements. One known method to stabilize catheters includes suturing the catheter to the user's skin. This intrusive method has obvious disadvantages such as increased infection risk, potential scaring from the suturing, and causing additional pain and discomfort to the user during and after the catheterization process. Many medical practitioners also utilize medical grade tape and/or commercially available "dressings" having an adhesive bottom layer to secure the catheter to the user's body. Employing tape and/or dressings, however, have many disadvantageous. Many of these known devices and methods often do not provide a barrier for bacteria, nor do they permit sufficient fluid/moisture transfer from the catheter insertion site to the outside ambient environment. Further, many of these devices and methods also do not allow a user to adequately view the insertion site or ensure the integrity of the catheter stabilization device. Even more problematically, when the tape or dressing is needed or desired to be changed, the removal or attempted removal of the tape or dressing causes displacement of the catheter. In many instances, the displacement or dislodgment of the catheter causes pain or discomfort to the user, and may also require the medical practitioner to engage in a new catheterization process.

Some known devices and methods attempt to solve some of the above-described catheter-stability deficiencies by utilizing rigid plastic or metallic retaining members shaped and sized to surround a portion of the catheter, typically the hub or collar portion. As those of skill in the art will appreciate, catheters are made in various shapes and sizes depending on their use and/or application. As such, medical practitioners and/or medical treatment facility administrators are required to buy catheter stabilization devices for various corresponding catheters. Moreover, for emergency situations or other situations where time is of-the-essence, utilizing these rigid fasteners are commercially and medically impracticable. Even worse, if the wrong sized fastener is utilized, it could cause displacement of the catheter. Lastly, those fasteners made of a metallic material are also problematic as they are incompatible for use in some diagnostic machines, such as magnetic resonance imaging (MRI).

Some known medical dressings solely utilize the bond of adhesive material itself to a users' skin to retain the catheter. In addition to some of the above-described disadvantageous, these dressings cause an effect called "tenting," wherein a portion of the dressing does not adhere to the user's skin. The larger the tent results in a reduced dwell time and retention performance of the dressing. Therefore, the larger the catheter the reduced performance.

Therefore, a need exists to overcome the problems with the prior art as discussed above.

SUMMARY OF THE INVENTION

The invention provides a catheter stabilization device and method of use that overcomes the hereinafore-mentioned disadvantages of the heretofore-known devices and methods of this general type and that enables users to effectively, efficiently, and safely retain a catheter in a position on a user's body.

With the foregoing and other objects in view, there is provided, in accordance with the invention, a catheter stabilization device having a release liner coupled to a catheter stabilization member. The catheter stabilization member has a permeable first layer and a bottom surface having an adhesive interposed between the release liner and the first layer and includes an elongated continuous retention strip coupled to the first layer. The elongated continuous retention strip is of a deformably rigid material that is operably configured to have a first static state with a first shape, a dynamic state, generated by an external force, with a second shape different than the first shape, and a second static state, after removal of the external force, with the second shape in a fixed configuration to resist movement of a catheter to be superimposed by the continuous retention strip.

In accordance with a further feature of the present invention, the elongated continuous retention strip is centrally and longitudinally disposed along a retaining member length of the catheter stabilization member.

In accordance with another feature, an embodiment of the present invention includes the catheter stabilization member also having a permeable second layer coupled to the first layer, wherein the elongated continuous retention strip is encapsulated by the first and second layers of the catheter stabilization member.

In accordance with yet another feature, an embodiment of the present invention also includes the catheter stabilization member having a proximal end, a distal end, and a retaining member length, wherein the retaining member length is greater than a retention strip length defined by opposing terminal ends of the elongated continuous retention strip.

In accordance with an additional feature, an embodiment of the present invention also includes a dressing made with a permeable material having a bottom surface including an adhesive disposed thereon, wherein a first film portion of the dressing defines a substantially transparent first window surrounded by a stabilization border, and may also define a second window corresponding to a peripheral shape of the catheter stabilization member.

In accordance with a further feature of the present invention, the release liner uniformly overlays the bottom surfaces of the dressing and catheter stabilization member. Additionally, the dressing and catheter stabilization member are indirectly coupled together through the liner and a second film portion of the dressing.

In accordance with an additional feature, an embodiment of the present invention also includes the dressing further also having a second film portion disposed in and defining the second window.

In accordance with a further feature of the present invention, the dressing also defines a spatial partition surrounding the peripheral shape of the catheter stabilization member.

In accordance with yet another feature, an embodiment of the present invention also includes the dressing having a peripheral edge defining a discontinuous slit spanning from a location on the peripheral edge to a circular aperture, wherein the second window of the dressing is interposed between the first window of the dressing and the circular aperture to allow visibility of the catheter stabilization member.

In accordance with an additional feature of the present invention, the catheter stabilization member is of a polymeric material. In additional embodiments, the catheter retention strip is a color in contrast with an upper surface of the catheter retention member.

Also in accordance with the present invention, an advantageous combination is disclosed. This combination includes a catheter superimposed by a medical dressing of a permeable material, having a top surface, having a bottom surface adhesively coupled to skin of a human user, and having a portion defining a substantially transparent first window, wherein an improvement is disclosed that includes a catheter stabilization member interposed between the top surface of the medical dressing and the skin of a human user. The catheter stabilization member ash a bottom surface adhesively coupled to the skin of a human user and includes an elongated continuous retention strip of a flexible and deformably rigid material in a configuration generally contouring an exposed surface of the catheter.

In accordance with yet another feature, an embodiment of the present invention also includes the catheter stabilization member also having a permeable first layer with the elongated continuous retention strip coupled to the first layer, wherein the elongated continuous retention strip is disposed within the first window.

In accordance with yet another feature, an embodiment of the present invention also includes the medical dressing having a first film portion defining the substantially transparent first window surrounded by a stabilization border and also includes a second film portion defining a second window. The improvement includes the catheter stabilization member having a peripheral shape of corresponding to the second window, wherein the catheter stabilization member is structurally unattached to the medical dressing.

Also in accordance with the present invention, a method of utilizing a variable-sized catheter stabilization device is disclosed that includes the steps of (1) providing a catheter, (2) providing a catheter stabilization member with a bottom surface having an adhesive and with an elongated continuous retention strip of a flexible and deformably rigid material, (3) deforming the shape of the elongated continuous retention strip to a fixed configuration substantially contouring and superimposing an exposed surface of the catheter, and (4) fastening the bottom surface of the catheter stabilization member to secure the catheter to a user's skin.

In accordance with yet another feature, an embodiment of the present invention also includes providing a permeable medical dressing defining a first substantially transparent window with a bottom surface having an adhesive and superimposing the catheter stabilization member with the permeable medical dressing such that the elongated continuous retention strip of the catheter stabilization member is disposed within the first substantially transparent window of the permeable medical dressing.

In accordance with yet another feature, another embodiment of the present invention also includes removing the permeable medical dressing without dislodging the catheter stabilization member.

Although the invention is illustrated and described herein as embodied in a catheter stabilization device and method of use, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the catheter stabilization device spanning a length of the catheter stabilization device traversing the catheter from the distal end to the proximal end of the catheter stabilization device.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 4a depicts an exemplary catheter tip;

FIG. 4b depicts an elevational side view of the catheter stabilization device of FIG. 4c, with a release liner coupled thereto;

FIG. 4c depicts the catheter stabilization device of FIG. 4b superimposing the catheter of FIG. 4a;

FIGS. 6a-c depict various steps in an exemplary method of securing a catheter in accordance with one embodiment of the present invention; and FIG. 7 is a process flow diagram depicting a method of utilizing a variable-sized catheter stabilization device in accordance with one embodiment of the present invention.

DETAILED DESCRIPTION OF THE INVENTION

Figure 1:
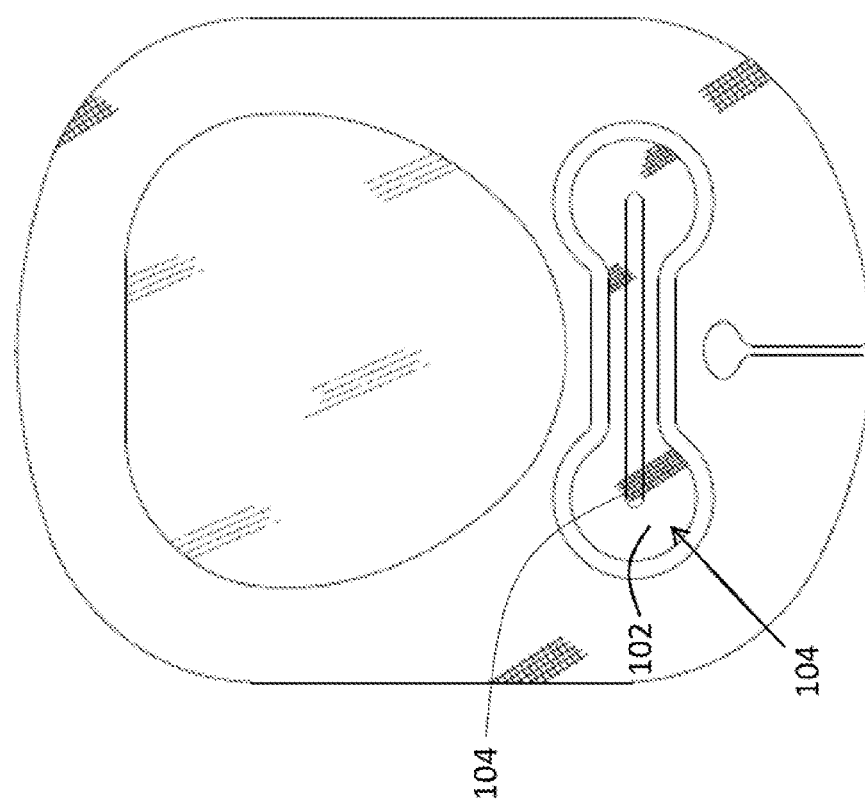
FIG. 1 is an elevational top plan view of a catheter stabilization system in accordance with one embodiment of the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient catheter stabilization device or assembly. As discussed above, the term "catheter" may include those devices traditionally known as "catheters," in addition to vascular access devices, as described above, and other similar devices. Embodiments of the invention provide stabilization for a catheter at least through a catheter stabilization device having a deformably rigid strip, wherein the strip may be deformed or modified in shape to substantially contour a catheter. Unlike those known devices and methods, the deformably rigid strip is operable to remain in said contour or shape and provides effective retention of said catheter not accomplished with the prior art. Advantageously, the stabilization device is permeable to allow moisture vapor transfer to occur and may also be embodied in a permeable medical dressing with one or more substantially transparent window (s) to effectively view a catheter insertion site and/or the retention of the catheter stabilization device, and safely reduce moisture accumulation under the dressing or catheter stabilization device, as described below.

Figure 2:
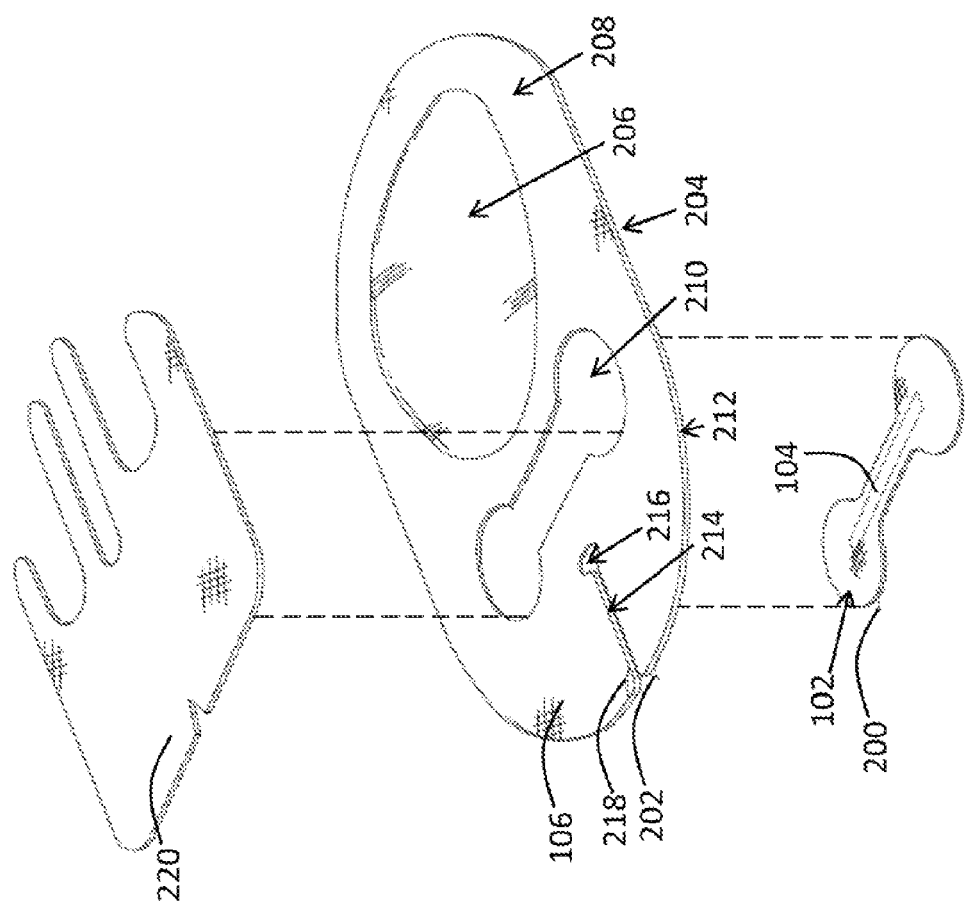
FIG. 2 is an exploded view of a catheter stabilization device, a medical dual transparent dressing, and a secondary catheter stabilization member in accordance with one embodiment of the present invention.
Figure 3:
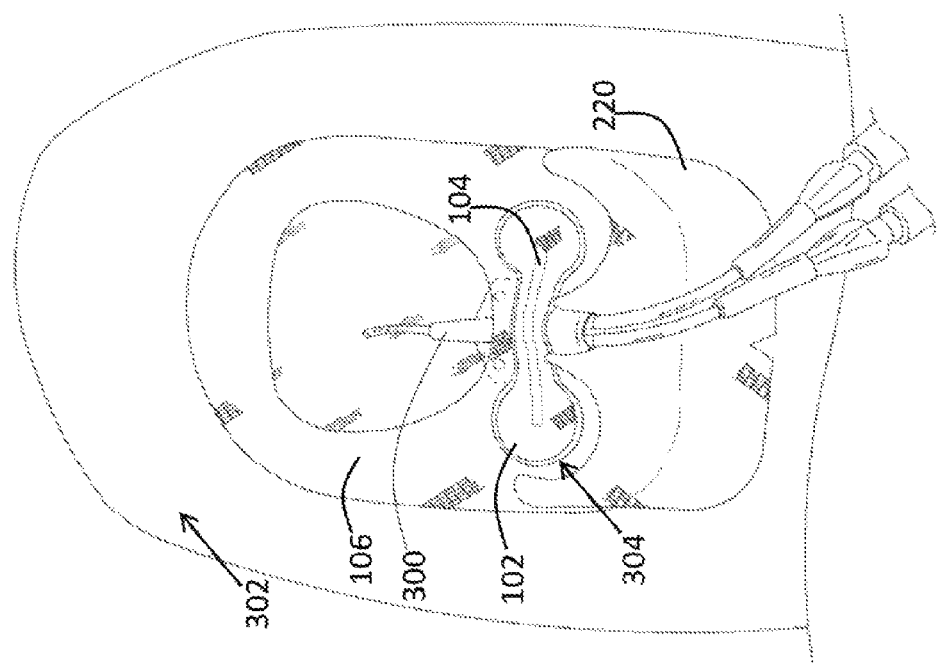
FIG. 3 is a perspective view of the catheter device coupled to a user in accordance with the present invention.

Referring now to FIGS. 1-2, one embodiment of the present invention is shown in a top plane view and exploded view, respectively. FIGS. 1-2 show several advantageous features of the present invention, but, as will be described below, the invention can be provided in several shapes, sizes, combinations of features and components, and varying numbers and functions of the components. The first example of a catheter stabilization system 100 includes a release liner 200 and a catheter stabilization member 102 with an elongated continuous retention strip 104 coupled thereto. The device 100 may also include a medical dressing 106 that may embody the catheter stabilization member 102. As shown in FIG. 2, the catheter stabilization system 100 may also include a secondary catheter stabilization member 220. Advantageously, the continuous retention strip 104 is of a deformably rigid material operably configured to be variably sized to substantially contour, and then retain its contoured shape to hold a catheter 300, as depicted in FIG. 3.

Figure 4:
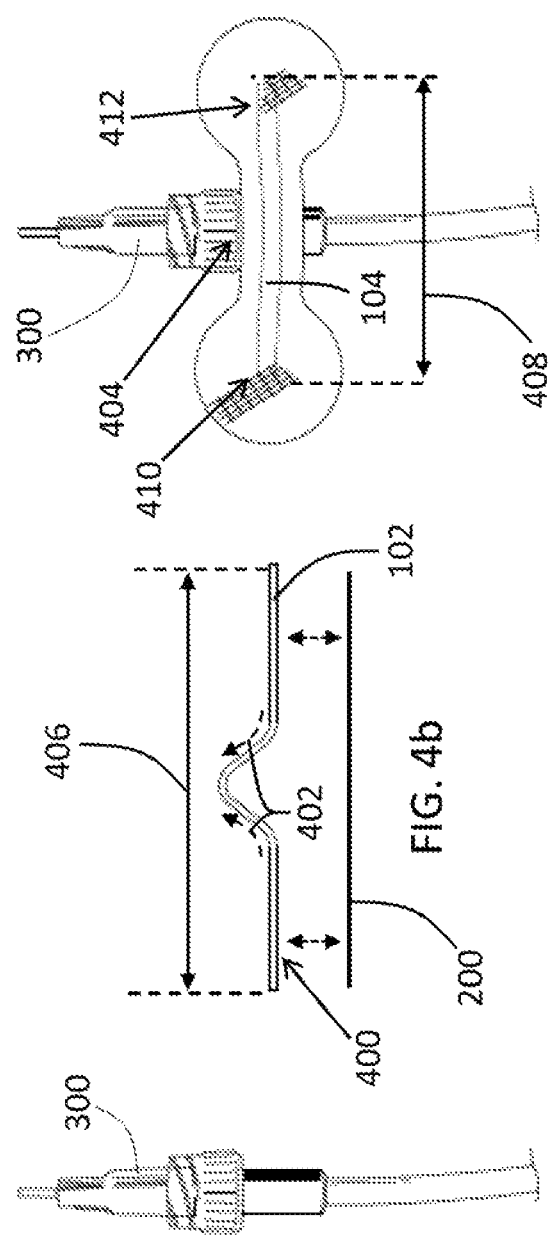

In one embodiment, the retention strip 104 is elongated, having a length to width aspect ratio greater than 1:1, as shown in FIG. 1. In other embodiments, the aspect ratio is less than 1:1, but is of a sufficient length to substantially contour the catheter and retain it. The material of the strip 104 is "deformably rigid" in that it allows a user to deform its shape and/or size, and yet retain the structural rigidity of that material when placed in said modified shape and/or size. Said differently, the material is rigid, yet has shape memory properties. As such, the commonly known tenting effect found in most known dressings is reduced, if not eliminated entirely. With brief reference to FIGS. 2 and 4, the strip 104 may also be said to have a first static state with a first shape, as shown in FIG. 2. This exemplary first static state may be the shape the strip 104 is initially manufactured in, and sold to the user. When used, it holds and retains its shape as shown in FIG. 4b.

As shown in FIG. 2, the strip 104 is planar and rectangular. In one embodiment, the strip 104 is polyethylene having an ASTM D638 tensile modulus of 0.1-2 ($10^5$ psi), an ASTM D790 flexural modulus of 0.08-2 ($10^5$ psi), and an ASTM D638 elongation of 20-1000%, depending on whether the polyethylene is low or high density. Other polymeric materials may be utilized. The material of the strip 104 advantageously permits clinicians the ability to perform diagnostic testing on the user with the catheter stabilization system 100 still retained and without affecting the operation of or results from diagnostic machine. In other embodiments, the material of the strip may be a nickel-titanium alloy. In further embodiments, the strip 104 may be slender in relation to the stabilization member to which it is coupled. The strip 104 may be free of protrusion spanning its length so as to make it substantially rectangular. The strip 104 may also be formed in a distinguishing color or texture relative to the color of an upper surface of the stabilization member 102 to effectively indicate to the user viewing the strip, from above the site where it is to be attached, where to apply the deforming force. In one embodiment, the strip 104 is black, while the entire upper surface of the member 102 is white. Other contrasting colors may be utilized and essentially the contrast in colors can be any two colors having a visually discernable difference by a user, and the entire surface does not have to be contrasting in color.

As discussed above, the catheter stabilization member 102 may have a film or release liner 200 that is required to be removed and a bottom surface 400 with an adhesive disposed thereon. In one embodiment, the adhesive may be a pressure sensitive adhesive (PSA) that is acrylate-based. In other embodiments, the adhesive may be hydrocolloid-based, an epoxy, or another adhesive.

When a catheter 300 is desired to be retained to the user, the catheter stabilization member 102 is placed in a dynamic state, generated for example by an external force, e.g., a compression force by a user's fingers. As shown in FIG. 4b, the dynamic state causes a second shape different than the first shape. An exemplary motion of the member 102 in the dynamic state is depicted in FIG. 4b with arrows 402. After removal or release of the external force, the material of the strip 104 is in the fixed configuration with respect to the second shape. Said another way, the strip 104 is in a configuration generally contouring an exposed surface 404 of the catheter 300. The term "generally contouring" is defined as surrounding the sides of an object in at least two directional axes. For example, as shown in FIG. 4c, the strip 104 can be seen spanning upwardly, and having a vertical-axis component, on the left exposed surface of the catheter 300, then spanning in a horizontally, and having a horizontal-axis component, across a top exposed surface of the catheter, and then spanning downwardly, and having a vertical-axis component, on the right exposed surface of the catheter.

In most instances, the catheter stabilization member 102 is in a constant coupling configuration with the catheter 300, thereby providing resistance to lateral movement of the left, top, and right exposed surfaces of the catheter while in the second shape. When placed against a protruding feature, like a catheter hub, the retention strip 104 prevents the catheter 300 from moving longitudinally when the medical tubing is pulled or tugged. In other embodiments, there may be a small space between the exposed surfaces and the catheter stabilization member 102. As shown in FIG. 4b, the second shape of the strip 104 is in a rectangular and curvilinear profile. As such, the catheter stabilization member 102 reduces catheter migration or dislodgement typically generated by many of those known catheter stabilization or retention devices.

In some embodiments of the present invention, a portion of the member 102 and/or strip 104 along a longitudinal length 406 of the catheter stabilization member 102, defined by the opposing ends of the member 102, takes on, or corresponds with, the shape of the exposed surfaces of the catheter, i.e., those surfaces not in contact with a user's skin. As such, the catheter 300 may be prohibited or substantially inhibited from dislodging during a user's movements or upon being subjected to external forces. In one embodiment, when the catheter stabilization member 102 is in the first shape, the length 406 of the member 102 is approximately 64 mm and the length of the strip 104 is approximately 45 mm. When placed in the second shape, the length 406 of the member 102 is approximately 54 mm and the length of the strip 104 is approximately 35 mm. In other embodiments, the lengths of the catheter stabilization device and strip 104 may vary.

Figure 5:
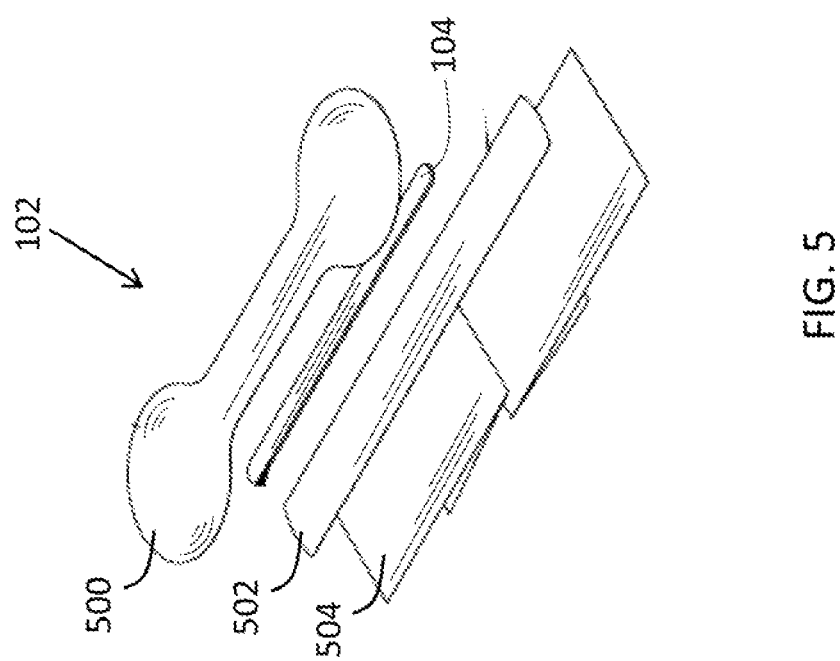
FIG. 5 is an exploded view of an exemplary catheter stabilization device in accordance with one embodiment of the present invention.

In one embodiment, the catheter retention member 102 is a permeable laminate consisting of various layers of material. With brief reference to FIG. 5, the catheter stabilization member 102 may include a permeable first layer 500 made with a polyethelyne foam, rayon acetate, or another material polymeric or fabric material. Advantageously, the elongated continuous retention strip 104 is coupled to the first layer by means of an adhesive or other fastener, and may be disposed on the upper surface of the first layer 500, the bottom surface of the first layer 500, or encapsulated therein. While an exemplary length of the strip 104 was discussed above, the width and thickness of the strip 104 may be approximately 2.5 mm and 0.4 mm, respectively. Variations outside of those dimensions may be modified in accordance with design applications and manufacturing constraints, as will be appreciated by those of skill in the art. In other embodiments, the catheter stabilization member 102 may include a nonwoven second layer 502 with an adhesive (as discussed above) disposed thereon, wherein one or more release liners 504 may be attached thereto. Those of skill in the art will also appreciate that the bottom surface of the catheter stabilization member 102 will vary based on the amount of layers utilized. As such, in one embodiment, the strip 104 and second layer 502, including its bottom surface, of the catheter stabilization member 102 are interposed between the release liner 504 and the first layer 500. Each the layers 500, 502 may be permeable, in that they permit the transfer of moisture vapor, from the catheter insertion or placement site, through the layers, to the ambient environment.

With reference to FIGS. 3-4, the elongated continuous retention strip 104 can be seen centrally and longitudinally disposed along a retaining member length 406 of the catheter stabilization member 102. As such, the catheter 300 can be evenly retained through the adhesive on the bottom surface of the catheter stabilization member 102. The catheter retention strip 104 can also be seen having a length 408 defined by opposing terminal ends 410, 412 of the elongated continuous retention strip 104. To provide a catheter stabilization member 102 that is flexible and effectuates a significant bond with a user's skin 302, the retention strip length 408 is less than the retaining member length 406. Said another way, the retaining member length 406 is greater than the retention strip length 408. In other embodiments, the strip 104 may span the entire length 406 of the stabilization member 102.

As described above, the catheter stabilization system 100 may also employ the use of a dressing 106 of a permeable material to further retain the catheter 300 and permit moisture vapor transfer from the catheter insertion site to the ambient environment. With reference now to FIGS. 2-3, the dressing 106 includes a bottom surface 204 with an adhesive disposed thereon, wherein the adhesive is superimposed with a release liner 202. The medical dressing 106 may also be a laminate consisting of various layers of material. In one embodiment, the dressing 106 has an upper dressing film 218, approximately 0.2 mm in thickness, defining a substantially transparent first window 206. The film 218 and/or window 206 may be substantially transparent, as they permit the user to effectively view the catheter insertion site. The entire film 218 and/or window 206 may be transparent or may be transparent in sections. Furthermore, the film 218 and/or window 206 may be translucent. The film 218 may be comprised of polyurethane or other material, as one of skill in the art can appreciate.

The film may be superimposed on and coupled to a nonwoven material, also having a 0.2 mm thickness. The nonwoven material creates a stabilization border 208 and may also have a bottom surface with an adhesive disposed thereon for coupling to a user's skin 302. In one embodiment, the dressing 106 defines a substantially transparent second window 210 corresponding to a peripheral shape of the catheter retention member 102. The second window 210 may also be defined by the film 218 superimposed on the nonwoven material or separate film superimposed on the dressing 106, also referred to herein as the second film portion. The film 218 and/or second film portion can also be said to indirectly couple the dressing 106 to the catheter stabilization member 102. The permeable first layer 500 of catheter securement member 102 is of a low surface energy material such that removal of the dressing 106, which may be indirectly coupled to the catheter stabilization member 102, does not dislodge or remove the catheter stabilization member 102 away from skin. Said another way, the adhesive bond with the catheter retention member 102 is greater than the adhesive bond between the film 218 and the top surface of the catheter retention member 102. In one embodiment, principally when the catheter stabilization member 102 and dressing 106 are initially sold embodied together, the release liner 202 of the dressing 106 uniformly overlays the bottom surfaces of the dressing 106 and catheter stabilization member 102. The second window 210 permits the user to view the catheter stabilization member 102 to ensure device is not damaged or soiled.

The dressing 106 also defines a spatial partition 304 surrounding the peripheral shape of the catheter stabilization member 102. Said another way, the second window 210 is sized and shaped to provide a continuous gap separating the stabilization member 102 and the dressing 106. As such, when the dressing 106 needs to be removed, repositioned, and/or replaced, the removal of the dressing 106 does not affect the configuration or placement of the catheter retention member 102. Said another way, the dressing 106 and catheter retention member 102 are indirectly coupled together through the liner 202. As such, the dressing 106 and catheter retention member 102 are structurally unattached or directly coupled with one another so as to provide removal of one without the other. Therefore, the removal of the dressing 106 does not affect the secured retention of the catheter retention member 102.

With specific reference to FIG. 2, the dressing 106 can also be seen having a peripheral edge 212 defining a discontinuous slit 214 spanning from a location on the peripheral edge 212 to a circular aperture 216. The slit 214 and aperture 216 advantageously permit tubes, wires, or other devices to be routed through the dressing 106 and reach the catheter retention member 102 with minimal interference of the bond between the adhesive on the bottom surface of the dressing and the user's skin. The second window 210 is beneficially configured on the dressing 106 to be interposed between the first window 206 and the circular aperture 216.

FIGS. 6a-c will be described in conjunction with the process flow chart of FIG. 7 and depict a method of utilizing a variable-sized catheter stabilization device. Although FIGS. 6a-c and 7 show a specific order of executing the process steps, the order of executing the steps may be changed relative to the order shown in certain embodiments. Also, two or more blocks shown in succession may be executed concurrently or with partial concurrence in some embodiments. Certain steps may also be omitted in said figures for the sake of brevity. In some embodiments, some or all of the process steps included in FIG. 7 can be combined into a single process. For example, when then the stabilization member 102 and dressing 106 are coupled together through a liner, as described below, the removal of the liner will expose adhesive for attachment to a user. The process begins at step 700 and immediately proceeds to step 702 of providing a catheter, e.g., 600. Then, step 704 includes providing a catheter stabilization device that includes a catheter stabilization member 602 with a bottom surface having an adhesive and with an elongated continuous retention strip of a flexible and deformably rigid material.

Next, step 706 includes deforming the shape of the elongated continuous retention strip of the stabilization member 602, which coincidentally changes the overall shape of the stabilization member 602, to a fixed configuration substantially contouring and superimposing an exposed surface of the catheter 600. Depending on the amount of the external force, the strip of material may conform to the entire outer exposed surface of a portion of the catheter 600, e.g., hub, desired to be retained. The user may then remove one or more liners on the catheter stabilization member 602 or a dressing 604 utilized therewith to exposed adhesive disposed on one or more portions of the bottoms surfaces of the catheter stabilization member 602 and/or the dressing 604. Next, step 708 includes fastening the bottom surface of the catheter retention member 602 to secure the catheter 600 to a user's skin 606.

Again, if the device includes a dressing 604, as also described above, another step includes superimposing the catheter retention member 602 with the permeable medical dressing such that the elongated continuous retention strip of the catheter retention member 602 is disposed within a first substantially transparent window 608 of the permeable medical dressing 604. In other embodiments when the dressing 604 has two windows, or when the window is large enough, the dressing 604 will be superimposed such that the catheter 600 and retention member 602 are superimposed by the dressing 604. After the dressing 604 is applied, the process may also include, after the wires or tubes are inserted through the dressing 604, superimposing a secondary catheter stabilization member 610 on the dressing and/or the tubes/wires through adhesive disposed on the bottom surface of the secondary catheter stabilization member 610. As shown in FIGS. 2 and 6c, the secondary catheter stabilization member 610 includes slits or notches that are designed to receive tubes and/or wires and contour a portion of the peripheral shape of the catheter stabilization or retention member 602.

In another advantageous step, the process includes the step 710 of removing the permeable medical dressing 604 without dislodging the catheter stabilization member 602. The process may terminate at step 712.

A catheter stabilization system has been disclosed that provides stabilization for a catheter through a catheter stabilization device having a deformably rigid strip operably configured to deformably modify, and then retain a shape to substantially contour a catheter. The laminate of the catheter stabilization device is permeable and may also be embodied in a permeable medical dressing with one or more substantially transparent window(s) to effectively view a catheter insertion site and/or the deformably rigid strip, and safely reduce moisture accumulation under the catheter stabilization system.

What is claimed is:

1. A catheter stabilization device comprising:
   a release liner; and
   a catheter stabilization member with a permeable first layer and a bottom surface having an adhesive interposed between the release liner and the first layer, the catheter stabilization member having an elongated continuous retention strip coupled to the first layer, the elongated continuous retention strip of a deformably rigid material operably configured to have:
   a first static state with a first shape;
   a dynamic state, generated by an external force, with a second shape different than the first shape; and
   a second static state, after removal of the external force, with the second shape in a fixed configuration to resist movement of a catheter to be superimposed by the continuous retention strip, wherein the second shape is capable of being maintained without external support.

2. The catheter stabilization device according to claim 1, wherein:
the elongated continuous retention strip is centrally and longitudinally disposed along a retaining member length of the catheter stabilization member.

3. The catheter stabilization device according to claim 1, wherein the catheter stabilization member further comprises:
a permeable second layer coupled to the first layer, wherein the elongated continuous retention strip is encapsulated by the first and second layers of the catheter stabilization member.

4. The catheter stabilization device according to claim 3, wherein:
the elongated continuous retention strip is centrally disposed along a longitudinal length of the catheter stabilization member.

5. The catheter stabilization device according to claim 1, further comprising:
a dressing of a permeable material, with a bottom surface including an adhesive disposed thereon, with a first film portion defining a substantially transparent first window surrounded by a stabilization border, and defining with a second window corresponding to a peripheral shape of the catheter stabilization member.

6. The catheter stabilization device according to claim 5, wherein:
the release liner uniformly overlays the bottom surfaces of the dressing and catheter stabilization member.

7. The catheter stabilization device according to claim 5, wherein the dressing further comprises:
a second film portion disposed in and defining the second window.

8. The catheter stabilization device according to claim 7, wherein:
the dressing and catheter stabilization member are indirectly coupled together through the liner and the second film portion.

9. The catheter stabilization device according to claim 5, wherein the dressing further comprises:
a peripheral edge defining a discontinuous slit spanning from a location on the peripheral edge to a circular aperture, wherein the second window of the dressing is interposed between the first window of the dressing and the circular aperture to allow visibility of the catheter stabilization member.

10. The catheter stabilization device according to claim 1, wherein:
the elongated continuous retention strip is a color in contrast with an upper surface of the catheter retention member.

11. In combination with a catheter superimposed by a medical dressing of a permeable material, having a top surface, having a bottom surface adhesively coupled to skin of a human user, and having a portion defining a substantially transparent first window, an improvement comprising:
a catheter stabilization member interposed between the top surface of the medical dressing and the skin of a human user, the catheter stabilization member having a bottom surface adhesively coupled to the skin of a human user and including an elongated continuous retention strip of a flexible and deformably rigid material in a configuration generally contouring an exposed surface of the catheter, wherein said configuration of the elongated continuous retention strip is capable of being maintained without external support.

12. The combination according to claim 11, wherein the catheter stabilization member further comprises:
a first static state with a first shape in the configuration generally contouring the catheter;
a dynamic state, generated by an external force, with a second shape different than the first shape; and
a second static state, after removal of the external force, with the second shape in a fixed configuration.

13. The combination according to claim 11, wherein the catheter stabilization member further comprises:
a permeable first layer with the elongated continuous retention strip coupled to the first layer, wherein the elongated continuous retention strip is disposed within the first window.

14. The combination according to claim 11, wherein the medical dressing includes a first film portion defining the substantially transparent first window surrounded by a stabilization border and includes a second film portion defining a second window, the catheter stabilization member further comprising:
a peripheral shape of corresponding to the second window, wherein the catheter stabilization member is structurally unattached to the medical dressing.

15. The combination according to claim 14, wherein the medical dressing includes a peripheral edge defining a discontinuous slit spanning from a location on the peripheral edge to a circular aperture, the second window of the medical dressing interposed between the first window of the medical dressing and the circular aperture.

16. A method of utilizing a variable-sized catheter stabilization device, including the steps of:
providing a catheter;
providing a catheter stabilization member with a bottom surface having an adhesive and with an elongated continuous retention strip of a flexible and deformably rigid material;
applying an external force to deform the shape of the elongated continuous retention strip to a fixed configuration substantially contouring and superimposing an exposed surface of the catheter, said fixed configuration capable of being maintained without external support; and
fastening the bottom surface of the catheter stabilization member to secure the catheter to a user's skin.

17. A catheter stabilization device comprising:
a release liner;
a catheter stabilization member with a permeable first layer and a bottom surface having an adhesive interposed between the release liner and the first layer, the catheter stabilization member having an elongated continuous retention strip coupled to the first layer, the elongated continuous retention strip of a deformably rigid material operably configured to have:
a first static state with a first shape;
a dynamic state, generated by an external force, with a second shape different than the first shape; and
a second static state, after removal of the external force, with the second shape in a fixed configuration to resist movement of a catheter to be superimposed by the continuous retention strip; and
a permeable second layer coupled to the first layer, wherein the elongated continuous retention strip is encapsulated by the first and second layers of the catheter stabilization member.

18. A catheter stabilization device comprising:
a release liner;
a catheter stabilization member with a permeable first layer and a bottom surface having an adhesive interposed between the release liner and the first layer, the catheter stabilization member having an elongated continuous retention strip coupled to the first layer, the elongated continuous retention strip of a deformably rigid material operably configured to have:
a first static state with a first shape;
a dynamic state, generated by an external force, with a second shape different than the first shape; and
a second static state, after removal of the external force, with the second shape in a fixed configuration to resist movement of a catheter to be superimposed by the continuous retention strip; and
a dressing of a permeable material, with a bottom surface including an adhesive disposed thereon, with a first film portion defining a substantially transparent first window surrounded by a stabilization border, and defining with a second window corresponding to a peripheral shape of the catheter stabilization member.

19. In combination with a catheter superimposed by a medical dressing of a permeable material, having a top surface, having a bottom surface adhesively coupled to skin of a human user, and having a portion defining a substantially transparent first window, an improvement comprising:
a catheter stabilization member interposed between the top surface of the medical dressing and the skin of a human user, the catheter stabilization member having a bottom surface adhesively coupled to the skin of a human user;
elongated continuous retention strip of a flexible and deformably rigid material in a configuration generally contouring an exposed surface of the catheter; and
a permeable first layer with the elongated continuous retention strip coupled to the first layer, wherein the elongated continuous retention strip is disposed within the first window.

20. In combination with a catheter superimposed by a medical dressing of a permeable material, having a top surface, having a bottom surface adhesively coupled to skin of a human user, having a portion defining a substantially transparent first window, having a first film portion defining the substantially transparent first window surrounded by a stabilization border, and having a second film portion defining a second window, an improvement comprising:
a catheter stabilization member interposed between the top surface of the medical dressing and the skin of a human user, the catheter stabilization member having a bottom surface adhesively coupled to the skin of a human user, having a peripheral shape of corresponding to the second window, wherein the catheter stabilization member is structurally unattached to the medical dressing, and including an elongated continuous retention strip of a flexible and deformably rigid material in a configuration generally contouring an exposed surface of the catheter.

\* \* \* \* \*